United States Patent
Vander Meer et al.

(10) Patent No.: US 9,617,542 B2
(45) Date of Patent: *Apr. 11, 2017

(54) LEPIDOPTERAN MOTH CONTROL USING DOUBLE-STRANDED RNA CONSTRUCTS

(75) Inventors: Robert K. Vander Meer, Newberry, FL (US); Man-Yeon Choi, Gainesville, FL (US)

(73) Assignee: The United States of America, as representd by The Secretary of Agriculture, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/324,005

(22) Filed: Dec. 13, 2011

(65) Prior Publication Data

US 2012/0148525 A1 Jun. 14, 2012

Related U.S. Application Data

(60) Provisional application No. 61/422,721, filed on Dec. 14, 2010.

(51) Int. Cl.
| | |
|---|---|
| *C12N 15/82* | (2006.01) |
| *C12N 15/113* | (2010.01) |
| *A01N 57/16* | (2006.01) |
| *A01N 63/02* | (2006.01) |

(52) U.S. Cl.
CPC ......... *C12N 15/1136* (2013.01); *A01N 57/16* (2013.01); *A01N 63/02* (2013.01); *C12N 15/8286* (2013.01)

(58) Field of Classification Search
None
See application file for complete search history.

(56) References Cited

U.S. PATENT DOCUMENTS

| | | | | |
|---|---|---|---|---|
| 6,506,559 | B1 * | 1/2003 | Fire | A61K 31/7105 435/325 |
| 2009/0285784 | A1 * | 11/2009 | Raemaekers | A01N 57/16 424/93.2 |
| 2013/0305417 | A1 * | 11/2013 | Vander Meer | A01N 57/16 800/302 |

OTHER PUBLICATIONS

Ma et al, 1994, PNAS, 91:6506-6510.*
Asokan, 2008, Curr. Science, 94:1119.*
Yang et al, 2009, J. Appl. Entomol., 33:75-81.*
Lopez Jr. et al, 1994, J. Economic Entomology, 87:1653-1658.*
Bober et al, 2010, PNAS, 107:116858-16862.*

* cited by examiner

*Primary Examiner* — Jason Deveau Rosen
(74) *Attorney, Agent, or Firm* — John D. Fado; Mark D. McNemar (57) ABSTRACT

Disclosed is a dsRNA construct that relates to a method to control Lepidopteran moths via double-stranded RNA interference of the PBAN/Pyrokinin gene.

11 Claims, 3 Drawing Sheets

```
                              SEQUENCE LISTING

<160> NUMBER OF SEQ ID NOS: 14

<210> SEQ ID NO 1
<211> LENGTH: 585
<212> TYPE: DNA
<213> ORGANISM: Helicoverpa zea

<400> SEQUENCE: 1
atgttcaatc aaactcagtt gtttgttttt ctcgctgtat tcactacgag cagtgtttta     60
gggaataaca atgatgttaa ggatggcgca gcgagtggag ctcacagcga ccgactaggt    120
ctttggttcg gtcccggct  aggcaagcgc tcgctcagaa tatctaccga agataacaga    180
caagcattct tcaaattact cgaagccgcc gacgctttga aatactatta cgaccagcta    240
ccttatgaga tgcaagctga tgaacctgaa accagggtca ccaagaaggt gatcttcacc    300
cccaagttag gcagaagcct cgcatacgat gacaaaagct ttgagaacgt ggagttcacg    360
cccagactcg gcaggagact gtccgatgat atgcctgcca ccccgctga  ccaggaaatg    420 taccgccaag accctgaaca gattgacagc aggacaaagt acttctcccc aaggctcggc    480
agaaccatga acttctcacc acgactcggc agggaactgt cttatgatat gatgccaaat    540
aaaatcaggg tagtcaggag tacaaacaaa acgcgatcaa cataa                    585

<210> SEQ ID NO 2
<211> LENGTH: 508
<212> TYPE: RNA
<213> ORGANISM: Helicoverpa zea

<400> SEQUENCE: 2
caaugauguu aaggauggcg cagcgagugg agcucacagc gaccgacuag gucuuugguu     60
cgguccccgg cuaggcaagc gcucgcucag aauaucuacc gaagauaaca gacaagcauu    120
cuucaaauua cucgaagccg ccgacgcuuu gaaauacuau uacgaccagc uaccuuauga    180
gaugcaagcu gaugaaccug aaaccagggu caccaagaag gugaucuuca ccccaaguu    240 aggcagaagc cucgcauacg augacaaaag cuuugagaac guggaguuca cgcccagacu    300
cggcaggaga cuguccgaug auaugccugc caccccgcu  gaccaggaaa uguaccgcca    360
agacccugaa cagauugaca gcaggacaaa guacuucucc ccaaggcucg gcagaaccau    420
gaacuucuca ccacgacucg gcagggaacu gucuuaugau augaugccaa auaaaaucag    480
gguagucagg aguacaaaca aaacgcga                                       508

<210> SEQ ID NO 3
<211> LENGTH: 508
<212> TYPE: RNA
<213> ORGANISM: Helicoverpa zea

<400> SEQUENCE: 3
guuacuacaa uuccuaccgc gucgcucacc ucgaguguc  cuggcugauc cagaaaccaa     60
gccaggggcc gauccguucg cgagcgaguc uuauagaugg cuucuauugu cuguucguaa    120
gaaguuuaau gagcuucggc ggcugcgaaa cuuuaugaua augcuggucg auggaauacu    180
cuacguucga cuacuuggac uuuggucca  gugguucuuc cacuagaagu  ggggguucaa    240
uccgucuucg gagcguaugc uacuguuuuc gaaacucuug caccucaagu gcgggucga    300
```

```
gccguccucu gacaggcuac uauacggacg gugggggcga cugguccuuu acauggcggu    360
ucugggacuu gucuaacugu cguccuguuu caugaagagg gguuccgagc cgucuuggua    420
cuugaagagu ggugcugagc cgucccuuga cagaauacua uacuacgguu uauuuuaguc    480
ccaucagucc ucauguuugu uuugcgcu                                      508

<210> SEQ ID NO 4
<211> LENGTH: 24
<212> TYPE: DNA
<213> ORGANISM: Helicoverpa zea

<400> SEQUENCE: 4
aagatgttca atcaaactca gttg                                           24

<210> SEQ ID NO 5
<211> LENGTH: 27
<212> TYPE: DNA
<213> ORGANISM: Helicoverpa zea

<400> SEQUENCE: 5
aaattatgtt gatcgcgttt tgtttgt                                        27

<210> SEQ ID NO 6
<211> LENGTH: 40
<212> TYPE: DNA
<213> ORGANISM: Helicoverpa zea

<400> SEQUENCE: 6
taatacgact cactataggg gtgtttgcat tgtgtaccgc                          40

<210> SEQ ID NO 7
<211> LENGTH: 40
<212> TYPE: DNA
<213> ORGANISM: Helicoverpa zea

<400> SEQUENCE: 7
taatacgact cactataggg tataggaagg ggttgatggc                          40

<210> SEQ ID NO 8
<211> LENGTH: 40
<212> TYPE: DNA
<213> ORGANISM: Helicoverpa zea

<400> SEQUENCE: 8
taatacgact cactataggg acgtaaacgg ccacaagttc                          40

<210> SEQ ID NO 9
<211> LENGTH: 40
<212> TYPE: DNA
<213> ORGANISM: Helicoverpa zea

<400> SEQUENCE: 9
taatacgact cactataggg tgctcaggta gtggttgtcg                          40

<210> SEQ ID NO 10
<211> LENGTH: 24
<212> TYPE: PRT
<213> ORGANISM: Helicoverpa zea

<400> SEQUENCE: 10

Asn Asp Val Lys Asp Gly Ala Ala Ser Gly Ala His Ser Asp Arg Leu
1               5                   10                  15
```

```
Gly Leu Trp Phe Gly Pro Arg Leu
            20

<210> SEQ ID NO 11
<211> LENGTH: 7
<212> TYPE: PRT
<213> ORGANISM: Helicoverpa zea

<400> SEQUENCE: 11

Val Ile Phe Thr Pro Lys Leu
1               5

<210> SEQ ID NO 12
<211> LENGTH: 18
<212> TYPE: PRT
<213> ORGANISM: Helicoverpa zea

<400> SEQUENCE: 12

Ser Leu Ala Tyr Asp Asp Lys Ser Phe Glu Asn Val Glu Phe Thr Pro
1               5                   10                  15

Arg Leu

<210> SEQ ID NO 13
<211> LENGTH: 33
<212> TYPE: PRT
<213> ORGANISM: Helicoverpa zea

<400> SEQUENCE: 13

Leu Ser Asp Asp Met Pro Ala Thr Pro Ala Asp Gln Glu Met Tyr Arg
1               5                   10                  15

Gln Asp Pro Glu Gln Ile Asp Ser Arg Thr Lys Tyr Phe Ser Pro Arg
            20                  25                  30

Leu

<210> SEQ ID NO 14
<211> LENGTH: 8
<212> TYPE: PRT
<213> ORGANISM: Helicoverpa zea

<400> SEQUENCE: 14

Thr Met Asn Phe Ser Pro Arg Leu
1               5
```

LEPIDOPTERAN MOTH CONTROL USING DOUBLE-STRANDED RNA CONSTRUCTS

CROSS-REFERENCE TO RELATED APPLICATION

This present application claims priority under 35 U.S.C. §119(e) to U.S. Provisional Ser. No. 61/422,721, which was filed on Dec. 14, 2010, and is hereby incorporated by reference.

FIELD OF THE INVENTION

This invention relates to a method to control *Helicoverpa zea* via double-stranded RNA interference of the PBAN/Pyrokinin gene.

BACKGROUND OF INVENTION

Insect pests cost the general public billions of dollars annually in losses. These losses include the expense of controlling insect pests as well as crop loss and property damage caused by the pests. *Helicoverpa zea* has the capacity to inflict devastating yield losses to agronomically important crops. Depending the type of plant the larva feeds on, the pest is known commonly as the cotton bollworm when it feeds on cotton or corn earworm when it feeds on corn. *Helicoverpa zea* is typically controlled through the use of pyrethroid and *Bacillus thuringiensis* (Bt) insecticides.

Chemical pesticides are the primary tools used to combat these insect pests. However, use of traditional chemical pesticides has disadvantages, including non-target effects on neutral or beneficial insects, as well as other animals. Chemical pesticide usage also can lead to chemical residue run-off into streams and seepage into water supplies resulting in ecosystem/environment damage. In addition, animals higher in the food chain are at risk when they consume pesticide contaminated crops or insects. The handling and application of chemical pesticides also presents exposure danger to the public and professionals, and could lead to accidental dispersal into unintended environmentally sensitive areas. In addition, prolonged chemical pesticide application may result in an insect population becoming resistance to a chemical pesticide. In order to control a traditionally chemical resistant-pest, new more potent chemical pesticides must be utilized, which in turn will lead to another resistance cycle. As such, there is a need in the art to control pest populations without the disadvantages of traditional chemical pesticides.

An approach to decrease dependence on chemical pesticides is by causing a specific gene(s) of the target-pest to malfunction by either over expression or silencing gene expression. The silencing approach utilizes RNA interference pathways to knockdown the gene of interest via double-stranded RNA. Double-stranded RNA (dsRNA) induces sequence—specific post-transcriptional gene silencing in many organisms by a process known as RNA interference (RNAi). RNAi is a post-transcriptional, highly conserved process in eukaryotes that leads to specific gene silencing through degradation of the target mRNA. The silencing mechanism is mediated by dsRNA that is homologous in sequence to the gene of interest. The dsRNA is processed into small interfering RNA (siRNA) by an endogenous enzyme called DICER inside the target pest, and the siRNAs are then incorporated into a multi-component RNA-induced silencing complex (RISC), which finds and cleaves the target mRNA. The dsRNA inhibits expression of at least one gene within the target, which exerts a deleterious effect upon the target.

Fire, et al. (U.S. Pat. No. 6,506,559) discloses a process of introducing RNA into a living cell to inhibit gene expression of a target gene in that cell. The RNA has a region with double-stranded structure. Inhibition is sequence-specific in that the nucleotide sequences of the duplex region of the RNA and of a portion of the target gene are identical. Specifically, Fire, et al. (U.S. Pat. No. 6,506,559) discloses a method to inhibit expression of a target gene in a cell, the method comprising introduction of a double-stranded ribonucleic acid into the cell in an amount sufficient to inhibit expression of the target gene, wherein the RNA is a double-stranded molecule with a first ribonucleic acid strand consisting essentially of a ribonucleotide sequence which corresponds to a nucleotide sequence of the target gene and a second ribonucleic acid strand consisting essentially of a ribonucleotide sequence which is complementary to the nucleotide sequence of the target gene. Furthermore, the first and the second ribonucleotide strands are separately complementary strands that hybridize to each other to form the said double-stranded construct, and the double-stranded construct inhibits expression of the target gene.

In using dsRNA in controlling a target insect, one method is to engineer a baculovirus to produce a dsRNA construct in vivo as disclosed in Liu, et al. (U.S. Pat. No. 6,846,482). Salient to Liu is contacting an insect with a recombinant baculovirus wherein a first ribonucleic acid sequence corresponds to at least a portion of at least one gene endogenous to the insect to control the insect. Given the advances made in the field of transfection efficiency and RNA interference, there is a need in the art to utilize RNA interference technology without using a baculovirus as a vector. Such a method would mediate control of a target-pest without depending on variables associated with a baculovirus, such as expression and transfection of dsRNA by the baculovirus.

To utilize RNA interference as a method to regulate gene expression for control, a specific essential gene needs to be targeted. Genes associated with neurohormones represent novel potential targets. One neurohoromone gene family is the pheromone-biosynthesis-activating neuropeptide (PBAN)/pyrokinin gene family. The PBAN/pyrokinin gene produces multiple peptides, each of which are defined by a similar 5-amino-acid C-terminal sequence (FXPRLamide) that is the active core fragment for these peptides as reported in Raina, A. K. and T. G. Kempe (1992). "Structure activity studies of PBAN of *Helicoverpa zea* (Lepidoptera: Noctuidae)." Insect Biochem Mol Biol 22 (3): 221-225. It was subsequently determined that the five C-terminal amino acids, FXPRLamide, represented the minimal sequence required for activity as reported in Raina, A. K. and T. G. Kempe (1992) id.; Fonagy, A., L. Schoofs, et al. (1992). "Functional cross-reactivities of some locusta myotropins and *Bombyx* pheromone biosynthesis activating neuropeptide." J Insect Physiol 38 (9): 651-657; Kuniyoshi, H., H. Nagasawa, et al. (1992). "Cross-activity between pheromone biosynthesis activating neuropeptide (PBAN) and myotropic pyrokinin insect peptides." Biosci Biotechnol Biochem 56 (1): 167-8; and Raina, A. K. and T. G. Kempe (1990). "A pentapeptide of the C-terminal sequence of PBAN with pheromonotropic activity." Insect Biochem 20 (8): 849-851.

To date, over 200 PBAN/pyrokinin family peptides including peptides deduced from 37 species PBAN/pyrokinin genes have been identified. While it is one of the largest neuropeptide families in insects, the physiological functions of the PBAN/Pyrokinin peptides are only partially known. Members of the PBAN/pyrokinin family have been shown to have a variety of functions in insects such as: 1) stimulate pheromone biosynthesis in female moths (Raina et al., 1989); 2) induce melanization in moth larvae (Matsumoto et al., 1990; Altstein et al., 1996); 3) induce embryonic diapause and seasonal polyphenism in moths (Suwan et al., 1994; Uehara et al., 2011); 4) stimulate visceral muscle contraction (Nachman et al., 1986; Predel and Nachman, 2001); 5) accelerate puparium formation in several flies (Zdarek et al., 1997; Verleyen et al., 2004); 6) terminate pupal diapause in heliothine moths (Sun et al., 2003; Xu and Denlinger, 2003).

As such there is a need in the art to investigative whether the PBAN/Pyrokinin pathway can be used to interfere with essential developmental and/or reproductive functions of the targeted insect pests and result in abnormal development and/or lack of reproduction.

Furthermore there is a need for novel control methods that would interfere with essential developmental and/or reproductive functions of species that do not have the undesirable characteristics of traditional chemical pesticides. To that end, there is a need to develop dsRNA constructs that are engineered to interfere with essential developmental and/or reproductive functions of specific pest insects that would overcome some of the disadvantages of using traditional pesticides.

BRIEF SUMMARY OF THE INVENTION

Disclosed herewith is a method for controlling *Helicoverpa zea*, the method comprising: constructing a double-stranded ribonucleic acid construct that is complementary to a gene that encodes an PBAN/Pyrokinin gene sequence, dissolving the double-stranded ribonucleic acid to form a solution, and contacting an effective amount of said solution to *Helicoverpa zea*, wherein RNA interference is induced and *Helicoverpa zea* mortality occurs.

In an embodiment of the invention, one strain of the double-stranded ribonucleic acid is complementary to the nucleotide sequence of SEQ. ID. NO. 2. In another embodiment of the invention, one strain of the double-stranded ribonucleic acid is complementary to the nucleotide sequence of SEQ. ID. NO. 3. In an embodiment of the invention, SEQ. ID. NO. 2 and SEQ. ID. NO. 3 form a complementary double-stranded ribonucleic acid construct.

In another embodiment of the invention the double-stranded ribonucleic acid construct is dissolved in water to form a solution. One aspect of the invention is the solution is applied to *Helicoverpa zea* bait material. In one embodiment, the bait material contains a phagostimulant. Another aspect of the invention is the double-stranded ribonucleic acid construct solution is applied topically to *Helicoverpa zea*.

Another embodiment of the invention, disclosed is a double-stranded ribonucleic acid (dsRNA) for inhibiting the expression of a pheromone-biosynthesis-activating neuropeptide/pyrokynin peptide in a cell, wherein said dsRNA comprises a sense strand comprising a first sequence and an antisense strand comprising a second sequence complementary to SEQ ID NO: 2, wherein said first sequence is complementary to said second sequence. One aspect of the invention is the double-stranded ribonucleic acid is expressed in a plant cell.

In another embodiment of the invention, for inhibiting the expression of a pheromone-biosynthesis-activating neuropeptide/pyrokynin peptide in a cell, wherein said dsRNA comprises a sense strand comprising a first sequence and an antisense strand comprising a second sequence complementary to SEQ ID NO: 3, wherein said first sequence is complementary to said second sequence. One aspect of the invention is the double-stranded ribonucleic acid is expressed in a plant cell.

BRIEF DESCRIPTION OF THE DRAWINGS

The present invention together with the disclosed embodiments may best be understood from the following detailed description of the drawings, wherein.

BRIEF DESCRIPTION OF THE SEQUENCES

SEQ. ID. NO. 1: ATGTTCAATCAAACTCAGTTGTTT-GTTTTTCTCGCTGTATTCACTACGAGCAGTGTTT TAGGGAATAACAATGATGTTAAGGATGGCGCAGC-GAGTGGAGCTCACAGCGACCGA CTAGGTCTTTG-GTTCGGTCCCCGGCTAGGCAAGCGCTCGCTCA-GAATATCTACCGAA
GATAACAGACAAGCATTCTTCAAATTACTCGAAGC-CGCCGACGCTTTGAAATACTAT TACGACCAGCTAC-CTTATGAGATGCAAGCTGATGAACCTGAAACCA-GGGTCACCAA
GAAGGTGATCTTCACCCCCAAGTTAGGCAGAAGC-CTCGCATACGATGACAAAAGCT TTGAGAACGTG-GAGTTCACGCCCAGACTCGGCAGGAGACTGTC-CGATGATATGCCT
GCCACCCCCGCTGACCAGGAAATGTACCGC-CAAGACCCTGAACAGATTGACAGCAG GACAAAG-TACTTCTCCCCAAGGCTCGGCAGAACCATGAACT-TCTCACCACGACTCGG
CAGGGAACTGTCTTATGATATGATGC-CAAATAAAATCAGGGTAGTCAGGAGTACAA ACAAAACGCGATCAACATAA is the PBAN/pyrokinin gene cDNA of *Helicoverpa zea*.

SEQ. ID. NO. 2: is a 5' to 3' construct forming one strand of the dsRNA product referred to as HezPBAN dsRNA construct.

SEQ. ID. NO. 2: CAAUGAUGUUAAGGAUGGCGCA-GCGAGUGGAGCUCACAGCGACCGACUAGGUCU UUGGUUCGGUCCCCGGCUAGGCAAGCGCUCG-CUCAGAAUAUCUACCGAAGAUAAC AGA-CAAGCAUUCUUCAAAUUACUCGAAGCCGC-CGACGCUUUGAAAUACUAUUACG
ACCAGCUACCUUAUGAGAUGCAAGCUGAUGAAC-CUGAAACCAGGGUCACCAAGAA GGUGAUCUU-CACCCCCAAGUUAGGCAGAAGCCUCGCAUAC-GAUGACAAAAGCUUU

GAGAACGUGGAGUUCACGCCCAGACUCGGCAG-GAGACUGUCCGAUGAUAUGCCUG CCAC-CCCCGCUGACCAGGAAAUGUACCGCCAAGAC-CCUGAACAGAUUGACAGCAG GACAAAGUACUUCUCCCCAAGGCUCGGCAGAAC-CAUGAACUUCUCACCACGACUC GGCAGGGAACU-GUCUUAUGAUAUGAUGCCAAAUAAAAUCA-GGGUAGUCAGGAGU ACAAACAAAACGCGA is the dsRNA sequence structure of PBAN/pyrokinin gene of *Helicoverpa zea*.

SEQ. ID. NO. 3: is a 3' to 5' construct forming one strand of the dsRNA product referred to as HezPBAN dsRNA construct.

SEQ. ID. NO. 3:
GUUACUACAAUUCCUACCGCGUCGCUCACCUCGAGUGUCGCUGGCUGAU

CCAGAAACCAAGCCAGGGGCCGAUCCGUUCGCGAGCGAGUCUUAUAGAU

GGCUUCUAUUGUCUGUUCGUAAGAAGUUUAAUGAGCUUCGGCGGCUGCG

AAACUUUAUGAUAAUGCUGGUCGAUGGAAUACUCUACGUUCGACUACUU

GGACUUUGGUCCCAGUGGUUCUUCCACUAGAAGUGGGGGUUCAAUCCGU

CUUCGGAGCGUAUGCUACUGUUUUCGAAACUCUUGCACCUCAAGUGCGG

GUCUGAGCCGUCCUCUGACAGGCUACUAUACGGACGGUGGGGCGACUG

GUCCUUUACAUGGCGGUUCUGGGACUUGUCUAACUGUCGUCCUGUUUCA

UGAAGAGGGGUUCCGAGCCGUCUUGGUACUUGAAGAGUGGUGCUGAGCC

GUCCCUUGACAGAAUACUAUACUACGGUUUAUUUUAGUCCCAUCAGUCC

UCAUGUUUGUUUUGCGCU

DETAILED DESCRIPTION OF THE INVENTION

Disclosed here are specific insect pest dsRNA constructs that target PBAN/Pyrokinin gene expression. Using dsRNA inhibiting expression of the PBAN/Pyrokinin gene as a means of interfering with critical functions of the PBAN/Pyrokinin gene peptide products, a novel method to develop nucleic acid control for pest management is disclosed.

Definitions

As used in the specification and claims, the singular form "a", "an" and "the" include plural references unless the context clearly dictates otherwise. For example, the term "a cell" includes a plurality of cells, including mixtures thereof.

The term "gene" refers to a DNA sequence involved in producing a polypeptide or precursor thereof. The polypeptide can be encoded by a full-length coding sequence or by any portion of the coding sequence, such as exon sequences. In one embodiment of the invention, the gene target is a PBAN/Pyrokinin gene of an insect.

The term "pheromone-biosynthesis-activating neuropeptide/pyrokynin peptide" for *Helicoverpa zea*, refer to four gene product peptides comprising:

(SEQ. ID. NO. 10)
NDVKDGAASGAHSDRLGLWFGPRL, (SEQ. ID. NO. 11)
VIFTPKL, (SEQ. ID. NO. 12)
SLAYDDKSFENVEFTPRL, (SEQ. ID. NO. 13)
LSDDMPATPADQEMYRQDPEQIDSRTKYFSPRL,
and (SEQ. ID. NO. 14)
TMNFSPRL.

The term "oligonucleotide" refers to a molecule comprising a plurality of deoxyribonucleotides or ribonucleotides. Oligonucleotide may be generated in any manner, including chemical synthesis, DNA replication, reverse transcription, polymerase chain reaction, or a combination thereof. The present invention embodies utilizing the oligonucleotide in the form of dsRNA as means of interfering with a critical developmental or reproductive process that leads to control. Inasmuch as mononucleotides are synthesized to construct oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide, which is capable of acting as a point of initiation of synthesis when placed under conditions in which primer extension is initiated. An oligonucleotide "primer" may occur naturally, as in a purified restriction digest or may be produced synthetically.

A primer is selected to be "substantially complementary" to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence is sufficiently complementary with the sequence of the template to hybridize and thereby form a template primer complex for synthesis of the extension product of the primer.

The term "double-stranded RNA" or "dsRNA" refers to two substantially complementary strands of ribonucleic acid. "Identity," as used herein, is the relationship between two or more polynucleotide sequences, as determined by comparing the sequences. Identity also means the degree of sequence relatedness between polynucleotide sequences, as determined by the match between strings of such sequences. Identity can be readily calculated (see, e.g., *Computation Molecular Biology*, Lesk, A. M., eds., Oxford University Press, New York (1998), and *Biocomputing: Informatics and Genome Projects*, Smith, D. W., ed., Academic Press, New York (1993), both of which are incorporated by reference herein). While there exist a number of methods to measure identity between two polynucleotide sequences, the term is well known to skilled artisans (see, e.g., *Sequence Analysis in Molecular Biology*, von Heinje, G., Academic Press (1987); and *Sequence Analysis Primer*, Gribskov., M. and Devereux, J., eds., M Stockton Press, New York (1991)). Methods commonly employed to determine identity between sequences include, for example, those disclosed in Carillo, H., and Lipman, D., *SIAM J. Applied Math*. (1988) 48:1073. "Substantially identical" as used herein, means there is a very high degree of homology (preferably 100% sequence identity) between the inhibitory dsRNA and the corresponding part of the target gene. However, dsRNA having greater than 90% or 95% sequence identity may be used in the present invention, and thus sequence variations that might be expected due to genetic mutation, strain polymorphism, or evolutionary divergence can be tolerated. Although 100% identity is preferred, the dsRNA may contain single or multiple base pair random mismatches between the RNA and the target gene, provided that the mismatches occur at a distance of at least three nucleotides from the fusion site.

As used herein, "target gene" refers to a section of a DNA strand of a double-stranded DNA that is complementary to a section of a DNA strand, including all transcribed regions, that serves as a matrix for transcription. The target gene is therefore usually the sense strand.

The term "complementary RNA strand" refers to the strand of the dsRNA, which is complementary to an mRNA transcript that is formed during expression of the target gene, or its processing products. "dsRNA" refers to a ribonucleic acid molecule having a duplex structure comprising two complementary and anti-parallel nucleic acid strands. Not all nucleotides of a dsRNA must exhibit Watson-Crick base pairs. The maximum number of base pairs is the number of nucleotides in the shortest strand of the dsRNA.

As used herein, the term "GFP dsRNA" refers to a control dsRNA construct. The green fluorescent protein (GFP) is commonly used as a reporter gene and was originally isolated from jellyfish and widely used as control in prokaryotic and eukaryotic systems.

"Small interfering RNA" or "siRNA" refers to a short double-strand of ribonucleic acid, approximately 18 to 30 nucleotides in length. The term "RNA interference" or "RNAi" refers to a cellular mechanism for the destruction of targeted ribonucleic acid molecules. Under endogenous conditions, RNAi mechanism operates when dsRNA is cleaved to siRNA via an enzyme, DICER. The siRNA is processed to a single strand of anti-sense ribonucleic acid and coupled with a protein complex named RISC. The antisense RNA then targets a complementary gene construct, such as messenger RNA that is cleaved by ribonuclease. While the examples infra discloses constructing dsRNA constructs via enzymatic techniques with the enzyme RNA polymerase, it is contemplated that siRNA can be constructed via RNA oligonucleotide synthesis such as those disclosed in Scaringe, S., Methods Enzymol., 2000, Vol. 317:3 and incorporated herein by reference.

As used herein, "knock-down" is defined as the act of binding an oligonucleotide with a complementary nucleotide sequence of a gene as such that the expression of the gene or mRNA transcript decreases. In an embodiment, knock-down of a PBAN/pyrokinin gene occurs via injection of a dsRNA that can have multiple negative effects on the target insect, such as incomplete metamorphosis to the adult stage and untimely death of the target insect. Evidence of dsRNA having a negative effect on a targeted insect includes incomplete eclosion.

The term "substantially single-stranded" when used in reference to a nucleic acid product means that the product molecule exists primarily as a single strand of nucleic acid in contrast to a double-stranded product which exists as two strands of nucleic acids which are held together by interstrand base pairing interactions.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like.

The term "corresponds to" as used herein means a polynucleotide sequence homologous to all or a portion of a reference polynucleotide sequence, or a polypeptide sequence that is identical to a reference polypeptide sequence. In contradistinction, the term "complementary to" is used herein to mean that the complementary sequence is homologous to all or a portion of a reference polynucleotide sequence. For example, the nucleotide sequence "TATAC" corresponds to a reference sequence "TATAC" and is complementary to a reference sequence "GTATA".

An "effective amount" is an amount sufficient to effect desired beneficial or deleterious results. An effective amount can be administered in one or more administrations. In terms of treatment, an "effective amount" is that amount sufficient to make the target pest non-functional by causing an adverse effect on that pest, including (but not limited to) physiological damage to the pest; inhibition or modulation of pest growth; inhibition or modulation of pest reproduction; or death of the pest. In one embodiment of the invention, a dsRNA containing solution is fed to a target insect wherein critical developmental and/or reproductive functions of said insect are disrupted as a result of ingestion.

The term "solvent" includes any liquid that holds another substance in solution. Examples of solvents include but are not limited to water and organic solvents such as acetone, ethanol, dimethyl sulfoxide (DMSO), and dimethylformamide (DMF).

The term "phagostimulant" refers to any substance that will entice the insect to ingest the dsRNA. For insects, suitable phagostimulants include but are not limited to syrups, honey, aqueous solutions of sucrose, artificial sweeteners such as sucralose, saccharin, and other artificial sweeteners, amino acids, and other proteins.

Methods which are well known to those skilled in the art may be used to construct expression vectors containing sequences encoding PBAN/Pyrokinin gene and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) Current Protocols in Molecular Biology, John Wiley & Sons, New York, N.Y.

While the examples provided wherein describe dsRNA constructs cloned from GenBank Accession No. U08109 (*Helicoverpa zea*), it is contemplated that when read in conjunction with the teaching disclosed herein, the construction of other dsRNA constructs targeting PBAN/pyrokinin gene sequences of other insect orders would be feasible to those skilled the in the art. For example, including but not limited to the PBAN/pyrokinin gene/amino acid sequences disclosed in Table 1, it is contemplated that a dsRNA construct targeting the species disclosed in Table 1 of known PBAN/pyrokinin genes would control that respective insect.

Additionally it is contemplated that a single dsRNA construct would be effective in controlling a plurality of insect species.

TABLE 1

| Insect Order | Species | GenBank Accession # |
|---|---|---|
| Lepidoptera | Helicoverpa zea | U08109 |
| | Helicoverpa assulta | U96761/AY052417 |
| | Helicoverpa armigera | AY043222 |
| | Heliothis virescens | AY173075 |
| | Agrotis ipsilon | AJ009674 |
| | Mamestra brassicae | AF044079 |
| | Spodoptera littoralis | AF401480 |
| | Spodoptera exigua | AY628764 |
| | Pseudaletia separate | P25271 (amino acid sequence only) |
| | Clostera anastomosis | AY786305 |
| | Orgyia thyellina | AB259122 |
| | Lymantria dispar | AAB32665 (amino acid sequence only) |
| | Antheraea pernyi | AY445658 |
| | Samia cynthia ricini | AY286544 |
| | Manduca sexta | AY172672 |
| | Bombyx mori | NM_001043856 |
| | Bombyx mandarina | J. Sericultural Science of Japan, 68: 373-379 |
| | Ascotis selenaria cretacea | AB308061 |
| | Adoxophyes. sp | AF395670 |
| | Plutella xylostella | AY904342 |
| Diptera | Drosophila melanogaster | AY047528 |
| | Drosophila mauritiana | EF386943 |
| | Drosophila sechellia | EF386942 |
| | Drosophila simulans | EF386941 |
| | Aedes aegypti | XM_001650839/ XM_001662162 |
| | Culex quinquefasciatus | XM_001847366 |
| | Anopheles gambiae | XM_307885 |
| Coleoptera | Tribolium castaneum | EFA11568 |
| Hymenoptera | Apis melifera | NM_001110712 |
| | Nasonia vitripennis | NM_001167725 |
| | Solenopsis invicta | FJ223176 |
| | Solenopsis richteri | GQ872200 |
| | Solenopsis geminata | GQ872197 |
| | Solenopsis pergandei | GQ872198 |
| | Solenopsis carolinenesis | GQ872199 |
| | Harpegnathos saltator | GL445232 |
| | Camponotus floridanus | GL439118 |
| | Linepithema humile | Unpublished data |
| Hemiptera | Acyrthosiphon pisum (pea aphid) | Gene ID: ACYPIG135047 |
| | Rhodnius prolixus | GU230851 |

Example 1

Constructing dsRNA Construct for *Helicoverpa zea*

Cloning and Sequencing of Hez-PBAN/Pyrokinin Gene from *Helicoverpa zea*

A mRNA was isolated from the dissected brain-subesophageal ganglion (Br-SGs) of the adult moths (*Helicoverpa zea*) by Micro Fast mRNA purification kit (Invitrogen), and used to synthesize cDNA with the GeneRacer cDNA synthesis kit (Invitrogen). Cloning the full length Hez-PBAN cDNA was carried out using Generacer kit (Invitrogen) as described by the manufacturer. The primers, 5'-AAGATGTTCAATCAAACTCAGTTG-3' (SEQ. ID. NO. 4) and 5'-AAATTATGTTGATCGCGTTTTGTTTGT-3' (SEQ. ID. NO. 5) were designed from the sequence registered on the GenBank (Accession number: U08109). PCR was performed with the following temperature program: 33 cycles at 95° C. for 30 s, 52° C. for 30 s, and 72° C. for 1 min. The PCR product was gel purified and cloned using TOPO TA cloning kit (Invitrogen) and sequenced. The obtained full-length sequence information was aligned and sequences compared with our partial sequence using DNA analysis software.

Construction of Hez-PBAN/Pyrokinin dsRNA Construct and dsGFP Control

To construct Hez-PBAN dsRNA PCR primer set was designed 5'-T7-appended: 5'-TAATACGACTCAC-TATAGGG GTGTTTGCATTGTGTACCGC-3' (SEQ. ID. NO. 6), and 5'-TAATACGACTCACTATAGGGTATAG-GAAG GGGTTGATGGC-3' (SEQ. ID. NO. 7), to amplify 508-bp of Hez-PBAN DNA, which serves as the template for dsRNA synthesis using the MEGAscript RNA kit (Ambion). For a negative control, a green fluorescence protein (GFP) dsRNA was purchased from Ambion or was synthesized from a 546-bp GFP DNA template amplified by these primers 5'-TAATACGACTCACTATAGGGACGTAAA CGGCCACA AGTTC-3' (SEQ. ID. NO. 8) and 5'-TAATACGACTCACTATAGGGTGCTCAGGTAGTG-GTTGTCG-3' (SEQ. ID. NO. 9) using the same kit as above. The length of Hez-PBAN dsRNA (SEQ. ID. NO. 1) was constructed from the full length of Hez-PBAN cDNA, 585-bp (SEQ. ID. NO. 2 and SEQ. ID. NO. 3).

Example 2

Hez-PBAN dsRNA Injected into Pupae and Adult *Helicoverpa zea* Bioassay

Figure 1:
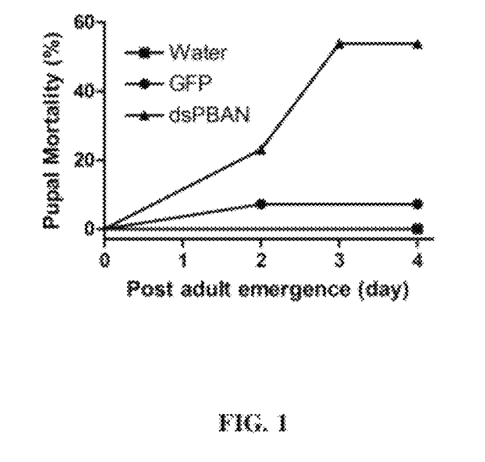
FIG. 1 is a graph depicting pupal mortality of *Helicoverpa zea* after PBAN dsRNA injection of HezPBAN dsRNA (1 µg/3 µL), water (3 µL), or GFP (1 µg/3 µL) injected into 4-5-day old female pupae (N=13).
Figure 2:
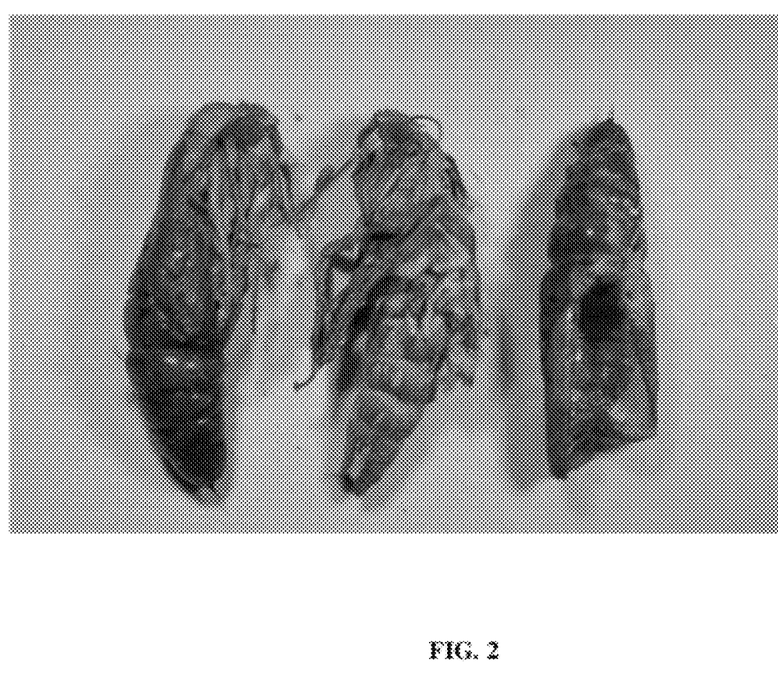
FIG. 2 is a photo depicting eclosion failure or problems for the adults leading to mortality from HezPBAN dsRNA injection. Data were analyzed by Kaplan-Meier survival curve comparison (PBAN vs. GFP & water, P=0.011 & 0.002, n≥13).

The dsRNA construct comprising the complementary strands of SEQ. ID. NO. 2 and SEQ. ID. NO. 3 was injected into 4 to 5 day old female pupae. Specifically 1 μg of Hez-PBAN dsRNA was injected into 13 female pupae and observed until adult emergence. For a control, 1 μg of GFP dsRNA as disclosed was injected into 13 female pupae. 3 μl of distilled water was also injected into 13 female pupae as an additional control. The pupae were then observed for mortality. As depicted in FIG. 1, it was observed that 53.8% of *Helicoverpa zea* pupae died as compared to 7.7% mortality and 0.5% mortality of dsRNA GFP and distilled water, respectively. This mortality was recorded as a failure of adult emergence as the pupae developed to adult tissue, but failed to escape from their cocoon as depicted in FIG. 2. Additionally, mortality was recorded as an event if the emerging *Helicoverpa zea* failed to expand their wings and appendages upon emergence.

Example 3

Inhibition of Pheromone Production via Hez-PBAN dsRNA in *Helicoverpa zea*

Pupae Bioassay

The dsRNA construct comprising the complementary strands of SEQ. ID. NO. 2 and SEQ. ID. NO. 3 was injected into *Helicoverpa zea* pupae. Specifically, 1 μg/3 μL of the dsRNA construct, water (3 μL), or GFP (1 μg/3 μL) was injected into female pupae as detailed in Example 2. Sex pheromone from female adults was then extracted 4-hr after light-off in the 2nd scotophase after adult emergence, then analyzed by via gas chromatography. The *Helicoverpa zea* pheromone glands were dissected at room temperature and soaked in a hexane solvent containing 100 ng cis-9-tetradecenal (Z9-14:Ald) as an internal standard. A gas chromatography (GC) 6890N (Agilent Technologies) equipped with a 30 m×0.25 mm DB-23 capillary column (J&W) was used to quantify the amount of cis-11-hexadecenal (Z11-16:Ald), a major sex pheromone component for *H. zea*. The gas chromatography oven temperature was programmed at 80°

Figure 3:
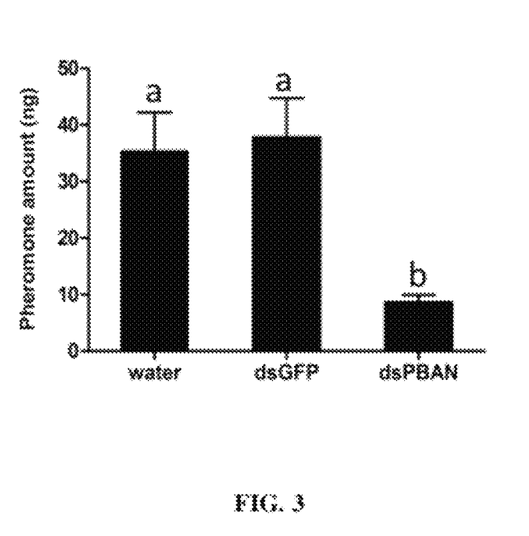
FIG. 3 is a graph depicting the effect of PBAN RNAi on sex pheromone production in *H. zea* female adults. HezPBAN dsRNA (1 µg/3 µL), water (3 µL) or GFP (1 µg/3 µL) was injected into 4-5-day old pupae. Sex pheromone was extracted 2-4 hr after light-off from 2-3-day old female adults. Bars with different letters are significantly different (unpaired t-test, two-tailed, PBAN vs. GFP & water, P=0.019 & 0.031, n≥5).

C. for 1 min, then 10° C./min to 230° C. and held for 8 min. As detailed in FIG. 3, pheromone production was reduced approximately 53% when compared against the water and GFP dsRNA controls.

While the invention has been described with reference to details of the illustrated embodiment, these details are not intended to limit the scope of the invention as defined in the appended claims.

The embodiment of the invention in which exclusive property or privilege is claimed is defined as follows:

1. An isolated double-stranded ribonucleic acid (dsRNA) for inhibiting the expression of a gene that encodes a pheromone-biosynthesis-activating neuropeptide/pyrokynin (PBAN) peptide in a cell consisting of sense strand SEQ ID NO: 2 with the sense strand being complementary to an antisense strand, wherein the dsRNA is capable of inducing RNA interference in *Helicoverpa zea*.

2. The dsRNA of claim 1, wherein the double-stranded ribonucleic acid is expressed in a transgenic plant cell.

3. A dsRNA for inhibiting the expression of a gene that encodes a pheromone-biosynthesis-activating neuropeptide/pyrokynin peptide in a cell consisting of sense strand SEQ ID NO: 3 with the sense strand being complementary to an antisense strand, wherein the dsRNA is capable of inducing RNA interference in *Helicoverpa zea*.

4. The double-stranded ribonucleic acid dsRNA of claim 3, wherein the double-stranded ribonucleic acid is expressed in a transgenic plant cell.

5. A method for controlling *Helicoverpa zea*, the method comprising: constructing a dsRNA that is complementary to a gene that encodes a PBAN/pyrokinin gene sequence wherein the dsRNA consists of SEQ ID NO: 2 or 3, with the sense strand being complementary to an antisense strand, dissolving the dsRNA to form a solution, and contacting at least one μg of dsRNA in said solution to *Helicoverpa zea*, wherein RNA interference is induced and *Helicoverpa zea* mortality occurs.

6. The method of claim 5, wherein the dsRNA construct is dissolved in water.

7. The method of claim 5, wherein the solution is incorporated in *Helicoverpa zea* bait material.

8. The method of claim 7, wherein the bait material contains a phagostimulant.

9. The method of claim 5, wherein the solution is applied topically to *Helicoverpa zea*.

10. The isolated dsRNA of claim 1, wherein the dsRNA is in solution.

11. The isolated dsRNA of claim 3, wherein the dsRNA is in solution.

\* \* \* \* \*